(12) United States Patent
Buelow et al.

(10) Patent No.: US 10,936,892 B2
(45) Date of Patent: Mar. 2, 2021

(54) DEVICE, SYSTEM AND METHOD FOR VERIFYING IMAGE-RELATED INFORMATION OF A MEDICAL IMAGE

(71) Applicant: KONINKLIJKE PHILIPS N.V., Eindhoven (NL)

(72) Inventors: Thomas Buelow, Grosshansdorf (DE); Tanja Nordhoff, Hamburg (DE); Stewart Young, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 114 days.

(21) Appl. No.: 16/076,905

(22) PCT Filed: Feb. 21, 2017

(86) PCT No.: PCT/EP2017/053953
§ 371 (c)(1),
(2) Date: Aug. 9, 2018

(87) PCT Pub. No.: WO2017/148751
PCT Pub. Date: Sep. 8, 2017

(65) Prior Publication Data
US 2019/0043195 A1 Feb. 7, 2019

(30) Foreign Application Priority Data
Feb. 29, 2016 (EP) ...................................... 16157840

(51) Int. Cl.
*G06K 9/03* (2006.01)
*G06T 7/00* (2017.01)
(Continued)

(52) U.S. Cl.
CPC ........... *G06K 9/036* (2013.01); *G06K 9/4628* (2013.01); *G06K 9/6202* (2013.01);
(Continued)

(58) Field of Classification Search
CPC ........ G06T 5/009; G06T 7/0012; G16H 30/20
See application file for complete search history.

(56) References Cited

U.S. PATENT DOCUMENTS

9,349,067 B2 * 5/2016 Kelly ....................... G06K 9/40
2003/0013951 A1 1/2003 Stefanescu et al.
(Continued)

*Primary Examiner* — Santiago Garcia (57) ABSTRACT

The present invention relates to device, system and method for verifying image-related information of a medical image. In order to assure the correctness of the image-related information of the medical image the device comprises an image input (21) for obtaining a medical image and associated image-related information, a translator (22) for translating one or more pieces of image-related information into expected anatomical feature information, a detector (23) for searching the expected anatomical feature information in the obtained medical image or for detecting one or more given anatomical features in the obtained medical image and comparing them with the expected anatomical feature information, an evaluator (24) for evaluating the result of the detector to generate a consistency measure indicating the consistency of the image-related information with the associated medical image, and an output interface (25) for outputting an inconsistency indication if the generated consistency measure is lower than a predetermined consistency threshold.

20 Claims, 3 Drawing Sheets

(51) Int. Cl.
*G06K 9/62* (2006.01)
*G06K 9/46* (2006.01)
*G16H 30/20* (2018.01)

(52) U.S. Cl.
CPC .......... *G06K 9/6271* (2013.01); *G06T 7/0012* (2013.01); *G06T 7/0014* (2013.01); *G16H 30/20* (2018.01); *G06K 2209/05* (2013.01); *G06T 2207/20081* (2013.01); *G06T 2207/20092* (2013.01); *G06T 2207/30168* (2013.01)

(56) References Cited

U.S. PATENT DOCUMENTS

| | | | |
|---|---|---|---|
| 2004/0057608 A1* | 3/2004 | Souluer | A61B 5/6843 382/128 |
| 2008/0267471 A1 | 10/2008 | Yu et al. | |
| 2010/0082692 A1 | 4/2010 | Akinyemi et al. | |
| 2010/0246912 A1* | 9/2010 | Periaswamy | G06K 9/00 382/131 |
| 2011/0110572 A1* | 5/2011 | Guehring | A61B 6/5258 382/131 |
| 2011/0188718 A1* | 8/2011 | Hill | G16H 30/20 382/128 |
| 2014/0016846 A1* | 1/2014 | Blaskovics | A61B 5/055 382/131 |
| 2015/0173701 A1 | 6/2015 | Major et al. | |
| 2015/0213646 A1* | 7/2015 | Ma | G06T 17/20 345/420 |
| 2016/0191887 A1* | 6/2016 | Casas | G02B 27/0172 348/47 |
| 2016/0328841 A1* | 11/2016 | Lay | G06T 7/337 |
| 2018/0060488 A1* | 3/2018 | Reicher | G16H 30/20 |
| 2018/0068070 A1* | 3/2018 | Keil | A61B 6/54 |
| 2018/0325481 A1* | 11/2018 | Young | A61B 6/50 |
| 2018/0326149 A1* | 11/2018 | Lipschultz | G16H 20/60 |
| 2020/0008768 A1* | 1/2020 | Young | A61B 6/5241 |

* cited by examiner

DEVICE, SYSTEM AND METHOD FOR VERIFYING IMAGE-RELATED INFORMATION OF A MEDICAL IMAGE

This application is the U.S. National Phase application under 35 U.S.C. § 371 of International Application No. PCT/EP2017/053953, filed on Feb. 21, 2017, which claims the benefit of European Application Serial No. 16157840.6, filed Feb. 29, 2016. These applications are hereby incorporated by reference herein.

FIELD OF THE INVENTION

The present invention relates to a device, system and method for verifying image-related information of a medical image.

BACKGROUND OF THE INVENTION

US 2011/0110572 A1 discloses a system for dynamically improving medical image acquisition quality. The system shall dynamically improve the quality of medical images using at least one processing device including an image analyzer, a correction processor and a message generator. The image analyzer automatically parses and analyzes data representing an image of a particular anatomical feature of a patient acquired by a medical image acquisition device to identify defects in the image by examining the data representing the image for predetermined patterns associated with image defects. The correction processor uses a predetermined information map associating image defects with corresponding corrective image acquisition parameters to determine corrected image acquisition parameters for use in re-acquiring an image using the image acquisition device in response to an identified defect. The message generator generates a message for presentation to a user indicating an identified defect and suggesting use of the corrected image acquisition parameters for re-acquiring an image.

Whenever a medical image, such as a radiological image, is acquired using a medical imaging device, additional information (i.e. associated image-related information), such as "body part examined", "image laterality", "view position", etc., is stored together with the image, e.g. in the DICOM (Digital Imaging and Communications in Medicine, a well known standard for handling, storing, printing, and transmitting information in medical imaging) header of the image before it is being stored, e.g. in a database, for instance by sending it to a PACS (Picture Archiving and Communication System). Typically, this additional image-related information is entered manually by a technologist.

Like all manually entered information, the aforementioned entries are prone to error. Once an image with erroneous image-related information is stored, such errors are hard to correct. In subsequent image viewing, e.g. according to specified hanging protocols, incorrect image-related information can lead to incorrect display of images and thus hamper the reviewing workflow.

US 2011/0188718 A1 discloses a system for admitting medical image data comprising image data and associated meta data, the system comprising input means arranged to receive image data from at least one source, a memory having stored therein consistency data defining at least one consistency criterion, and processing means arranged to analyze the image data to determine whether it meets the consistency criterion, and if it does not to amend the image data so that it does. Separate metadata matching and image matching is performed for determining a consistency with respect to a reference image.

SUMMARY OF THE INVENTION

It is an object of the present invention to provide a device, system and method for verifying image-related information of a medical image in order to assure the correctness of the image-related information of the medical image.

In a first aspect of the present invention a device for verifying image-related information of a medical image is presented, said device comprising:

an image input for obtaining a medical image and associated image-related information, a translator for translating one or more pieces of image-related information into expected anatomical feature information, a detector for searching the expected anatomical feature information in the obtained medical image or for detecting one or more given anatomical features in the obtained medical image and comparing them with the expected anatomical feature information, an evaluator for evaluating the result of the detector to generate a consistency measure indicating the consistency of the image-related information with the associated medical image, and an output interface for outputting an inconsistency indication if the generated consistency measure is lower than a predetermined consistency threshold.

In a further aspect of the present invention a system for verifying image-related information of a medical image is presented, said system comprising:

an image source for providing a medical image and associated image-related information and a device as disclosed herein for verifying image-related information of a medical image provided by the image source.

In a still further aspect of the present invention a corresponding method for verifying image-related information of a medical image is presented.

In yet further aspects of the present invention, there are provided a computer program which comprises program code means for causing a computer to perform the steps of the method disclosed herein when said computer program is carried out on a computer as well as a non-transitory computer-readable recording medium that stores therein a computer program product, which, when executed by a processor, causes the method disclosed herein to be performed.

Preferred embodiments of the invention are defined in the dependent claims. It shall be understood that the claimed method, computer program and medium have similar and/or identical preferred embodiments as the claimed system, in particular as defined in the dependent claims and as disclosed herein.

The present invention is based on the idea to perform an image analysis for analyzing the image content to check the consistency of the image content with the image-related information that has been provided by a user (e.g. the physician, a technologist, a nurse, etc.) or that has been associated with the image automatically, e.g. based on an automatic image analysis. If an inconsistency is detected, corresponding information is output. Said output information may be a kind of alert mechanism that functions like a spell-checker and draws the user's attention to possibly incorrect entries. The output information may also be control signal or trigger to repeat the detection, e.g. with different expected image-related information to check if it fits better with the medical image or not.

The inconsistency threshold used in the check may be predetermined and fixed, or may be individual to the kind of images. In an embodiment the user may also change or set the inconsistency threshold as desired. The consistency measure that is checked against the inconsistency threshold may thus be a number, such as an absolute number or a relative percentage, indicating how consistent the image-related information is with the associated medical image. For this check expected anatomical feature information is used, which is derived from the given image-related information and may e.g. be landmarks, distance information, size information, anatomical features, that are expected to be present in the medical image.

In an embodiment said detector is configured to generate a confidence measure indicating the confidence, with which one or more pieces of expected anatomical feature information have been detected in the obtained medical image or with which one or more given anatomical features in the obtained medical image correspond with the expected anatomical feature information, and wherein said evaluator is configured to use the generated confidence measure in the generation of the consistency measure. This improves the accuracy in determining the consistency measure.

To obtain even more precise results, said detector is configured to perform the detection separately for expected anatomical feature information from two or more pieces of image-related information to generate a confidence measure per piece of image-related information and wherein said evaluator is configured to combine the generated confidence measures for the generation of the consistency measure. Alternatively, said translator may be configured to separately translate each of two or more pieces of image-related information into separate pieces of expected anatomical feature information, wherein said detector is configured to perform the detection separately for two or more pieces of expected anatomical feature information to generate a confidence measure per piece of image-related information and wherein said evaluator is configured to combine the generated confidence measures for the generation of the consistency measure.

Various kinds of expected anatomical feature information may be used including the number and/or kind of anatomical features, expected image properties, distribution and/or location of one or more expected anatomical features, and/or variability in the spatial relations of one or more expected anatomical features. The translator may thus be configured configured to translate one or more pieces of image-related information into expected anatomical feature information including one or more of the number and/or kind of anatomical features, expected image properties, distribution and/or location of one or more expected anatomical features, and/or variability in the spatial relations of one or more expected anatomical features The device may further comprise a controller for controlling the detector and the evaluator to repeat their operations one or more times with different pieces of expected anatomical feature information if the generated consistency is lower than the predetermined consistency threshold or another predetermined consistency threshold. Said different pieces of expected anatomical feature information shall be related, but different to the first piece of expected anatomical feature information used in the first iteration. They may be selected arbitrarily or with a trained selector that evaluates the first piece of expected anatomical feature information for the selection. This provides for an increase in the correctness of the verification.

There are various options for the translator to obtain the necessary information for performing the translation of the one or more pieces of image-related information into expected anatomical feature information. In one embodiment said translator is configured to access a database storing separate expected anatomical feature information for a plurality of pieces of image-related information for translating one or more pieces of image-related information into expected anatomical feature information. In another embodiment said translator is configured to access a database storing the number and/or kind of anatomical features, expected image properties, distribution and/or location of one or more expected anatomical features, and/or variability in the spatial relations of one or more expected anatomical features. In still another embodiment said translator is configured to access a database storing separate expected anatomical feature information obtained by learning from training medical images and correctly associated image-related information.

The detection and evaluation may be repeated one or more times to find image-related information that better fits the medical image. Hence, in an embodiment said detector is configured to search alternative anatomical feature information in the obtained medical image or to detect one or more given anatomical features in the obtained medical image and compare them with alternative anatomical feature information, wherein said evaluator is configured to evaluate the result of the detector to generate an alternative consistency measure indicating the consistency of the alternative image-related information with the associated medical image, and wherein said output interface is configured to output an inconsistency indication if the previously generated consistency measure and the alternative consistency measure are lower than a predetermined consistency threshold.

It is also possible in a further embodiment to automatically check alternative hypotheses, e.g. if for a mammogram with view position "MLO" the confidence measure is low, alternative view positions "CC", "ML", . . . could be checked and suggested to the user, in case one of them matches better to the image data than the actual header information. This concept can be extended for other aspects, e.g. if in a head CT scan the confidence of the result of a head detector is low, alternative organ detectors could be applied to investigate whether the body part description in the image header was wrong.

The image input may be configured to obtain a medical image file comprising a data part including the medical image and a header including associated image-related information, in particular a medical image file in accordance with the DICOM standard. Generally, however, other file formats may be used as well.

The output interface may be configured to output an inconsistency indication in the form of an alert, in particular including the degree of inconsistency. The user may then check the image-related information and correct it.

Further options include that the image may be mapped to an anatomic atlas of the whole body which would then generate a hypothesis about which organ is in the image. This could then be explicitly checked using the detector, e.g. a dedicated organ detector. Different organ detectors may hereby be used for different organs. For a given organ the organ detector mentioned here can be the same as the one mentioned in claim one. Further, if the organ detector yields low confidence, organ-detectors for a pre-defined list of organs can be applied and the organ with the highest confidence would be suggested as body part. Still further, if the image information was related to view position, different standard view positions for the same organ can be tested.

The proposed system comprises an image source, which may be an imaging system, i.e. so that the acquired image is directly processed after acquisition and provision with additional image-related information, or an image database where the image (with or without the image-related information) is stored and checked for compliance with the image-related information at a later point in time.

The system may optionally further comprise one or more of a user interface for entering the image-related information, an output unit (e.g. a display, a controller, a transmission unit, etc.) for outputting the consistency information (e.g. an alert, a mere information, a control signal, etc.), and a database or storage holding the expected anatomical feature information. The system may comprise further elements and may be configured in various ways.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Figure 1:
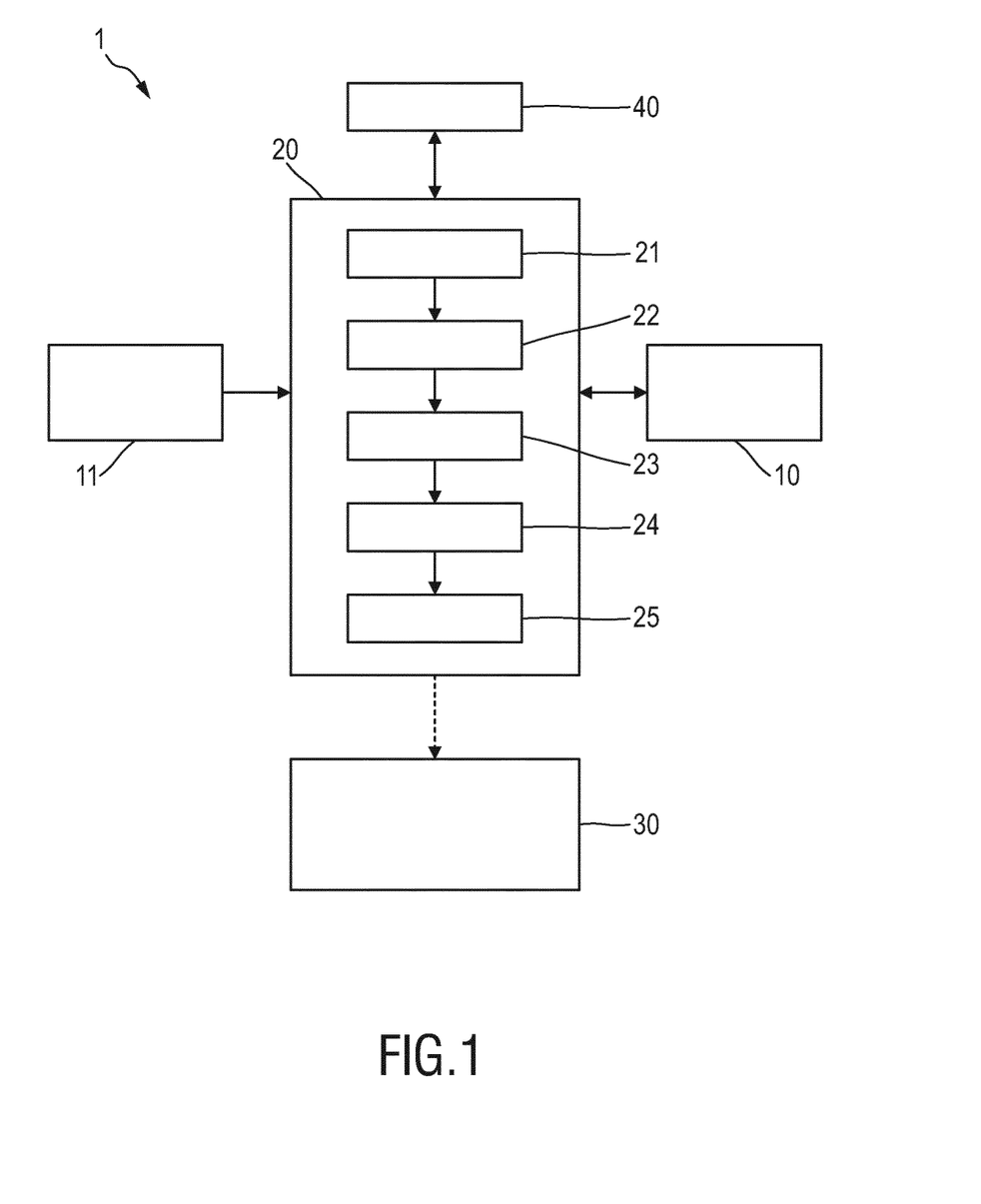
FIG. 1 shows a schematic diagram of a first embodiment of a system and a device according to the present invention.

FIG. 1 shows a schematic diagram of a first embodiment of a system 1 and a device 20 for verifying image-related information of a medical image according to the present invention. The system 1 comprises an image source for providing a medical image and associated image-related information. Said image source may be an image database or archive 10, such as a PACS, a hard-disk of a PC or workstation, an image repository of a hospital, etc. Alternatively, the image source may be an imaging system 11, such as a CT scanner, MR scanner, X-ray scanner, PET scanner, or image acquisition device of any other medical imaging modality.

The system 1 further comprises a device 20 for verifying image-related information of a medical image provided by the image source 10. The device 20 may e.g. be a processor of a PC or workstation that is coupled to or included in the imaging system 11, but may also be any other processing entity, such as a PC or workstation in a hospital network or of a physician, that is configured to perform the desired processing of a medical image. For instance, the device 20 may be provided somewhere in the path of a medical image between its acquisition by the imaging system 11 and its storage in an archive 10 such as the PACS so that it associated image-related information (entered e.g. by a physician, or caregiver, or nurse, or technologist) is verified before it is stored in the archive.

The image-related information may e.g. be information related to the imaging position of the subject (e.g. prone, supine, upright, etc.), the image body part (e.g. breast, hand, etc.), the view position (e.g. MLO (mediolateral oblique), CC (cranial-caudal), ML (mediolateral), etc.), laterality (e.g. right, left, etc.), the type of imaging system 11 (e.g. MR, CT, X-ray, etc.), parameters and settings of the image acquisition equipment (e.g. dose of radiation, duration, number of images, etc.). Other information may be alternatively or additionally included.

The device 20 comprises an image input 21 for obtaining a medical image and associated image-related information. The image input 21 may be data interface (e.g. a USB interface, WiFi interface, LAN interface, HDMI interface, etc.) for receiving or retrieving the medical image and associated image-related information, e.g. in a wireless or wired manner. For instance, each time new image-related information is entered or existing image-related information is modified, this image-related information and the associated medical image may automatically be sent to the image input for verification by the device 20.

The medical image and the associated image-related information may be stored in a common medical image file, wherein a data part includes the medical image and a header includes the associated image-related information. The medical image file may e.g. be formed in accordance with the DICOM standard.

The device 20 further comprises a translator 22 for translating one or more pieces of image-related information into expected anatomical feature information. Expected anatomical features may e.g. be landmarks, contours, shape descriptors, model pose, bones, vessel branches, etc. The relationship between image-related information and expected anatomical feature information may e.g. be learned from a set of correctly labeled training data, for a specific combination of modality, body part, view position, and/or laterality. Particularly image properties at a set of anatomical landmarks as well as the distribution of their locations and variability in the spatial relations between them can be learned. Thus, a trained algorithm may be used by the translator 22, or a look-up table storing the relationship between image-related information and expected anatomical feature information may be accessed for performing the translation.

The translator 22 may particularly be configured to translate one or more pieces of image-related information into expected anatomical feature information including the number and/or kind of anatomical features, expected image properties, distribution and/or location of one or more expected anatomical features, and/or variability in the spatial relations of one or more expected anatomical features.

For performing the translation the translator 22 may access a database 40 storing separate expected anatomical feature information for a plurality of pieces of image-related information for translating one or more pieces of image-related information into expected anatomical feature information. The database 40 may store the number and/or kind of anatomical features, expected image properties, distribution and/or location of one or more expected anatomical features, and/or variability in the spatial relations of one or more expected anatomical features. The database 40 may store separate expected anatomical feature information obtained by learning from training medical images and correctly associated image-related information.

The device 20 further comprises a detector 23 for searching the expected anatomical feature information in the obtained medical image or for detecting one or more given anatomical features in the obtained medical image and comparing them with the expected anatomical feature information. For this purpose one or more known detection algorithms may be used, e.g. a feature detection algorithm, a landmark detection algorithm or an organ detector. The detector may particularly be configured to detect the number and/or kind of anatomical features, expected image properties, distribution and/or location of one or more expected anatomical features, and/or variability in the spatial relations of one or more expected anatomical features.

The device 20 further comprises an evaluator 24 for evaluating the result of the detector to generate a consistency measure indicating the consistency of the image-related information with the associated medical image. Hereby, the evaluator 24 may particularly be configured to evaluate the detection result with respect to the number and/or kind of anatomical features, expected image properties, distribution and/or location of one or more expected anatomical features, and/or variability in the spatial relations of one or more expected anatomical features. Depending on said evaluation, e.g. on how many of the expected anatomical features have been found, how large the deviation of the location of landmarks is from their expect locations is, etc., the consistency measure is generated. For instance the number of expected anatomical features have been found is low and/or there are large deviations (e.g. above a deviation threshold), the consistency measure is higher than for the situation in which the number of expected anatomical features have been found is higher and/or there are small or no deviations (e.g. below a deviation threshold).

The device 20 further comprises an output interface 25 for outputting an inconsistency indication if the generated consistency measure is lower than a predetermined consistency threshold. The output interface 25 may e.g. be or included in a user interface such as a display or a loudspeaker to issue visual or audible information, but may also be an interface for transmitting information to another entity 30 in a wireless or wired manner, such as a WiFi or LAN interface, so that the inconsistency indication can be issued on said other entity 30, e.g. a workstation or PC of the person who entered the image-related information or a person responsible for monitoring or checking the correctness of image-related information and associated medical images. The inconsistency information may e.g. be issued in the form of an alert and may optionally include the degree of inconsistency.

The output interface 25 may further be configured in an embodiment to forward the received image-related information and associated medical image to the desired location, e.g. an image archive 10 (such as the PACS), if the image-related information has been verified as correct, e.g. if the generated consistency measure is higher than a predetermined consistency threshold.

Further, the output interface 25 may be configured in an embodiment to issue a consistency indication indicating that the image-related information has been verified as correct, e.g. if the generated consistency measure is higher than a predetermined consistency threshold. Such a consistency indication may be used by another entity, e.g. the image archive 10, to allow storage of the image-related information and associated medical image, or to mark them as verified in the archive 10.

Still further, in an embodiment, no such consistency indication is generated and issued, which may be interpreted, e.g. by the image archive 10, that the image-related information has been verified as correct.

The predetermined consistency threshold may be determined in advance and fixed. In other embodiments, it may be adapted by the user based on the desired level of correctness of the image-related information. Further, various thresholds may be used for different types of images, e.g. depending on the kind of imaging modality, or for different users, e.g. depending on the person or function of the person who entered the image-related information or who acquired the image using the imaging system 11.

In an embodiment the detector 23 does not only search the expected anatomical feature information in the obtained medical image or for detect one or more given anatomical features in the obtained medical image, but additionally generates a confidence measure indicating the confidence, with which one or more pieces of expected anatomical feature information have been detected in the obtained medical image or with which one or more given anatomical features in the obtained medical image correspond with the expected anatomical feature information. The evaluator 24 then uses the generated confidence measure in the generation of the consistency measure. If the confidence measure is higher the consistency measure is generally higher than in case the confidence measure is lower.

Preferably, the detector 23 performs the detection separately for two or more pieces of image-related information to generate a confidence measure per piece of image-related information. The evaluator 24 then combines the generated confidence measures for the generation of the consistency measure.

In an exemplary implementation the confidence measure is used as a second step after the anatomical feature detection. Based on the image-related information the anatomical feature detection will attempt to locate the expected anatomy (organ/body part) in the image and return the image location with the best fit. The confidence measure assesses the likelihood (e.g. on a scale from 0 to 1) that the identified location actually shows the expected anatomy, e.g., by evaluation the goodness of fit of an organ model. A low confidence value would then indicate that the expected organ is unlikely to be within the field-of-view.

Furthermore, the translator 22 may be configured to separately translate each of two or more pieces of image-related information into separate pieces of expected anatomical feature information, and the detector 23 may perform the detection separately for two or more pieces of expected anatomical feature information to generate a confidence measure per piece of image-related information. The evaluator 24 will then combine the generated confidence measures for the generation of the consistency measure.

Figure 2:
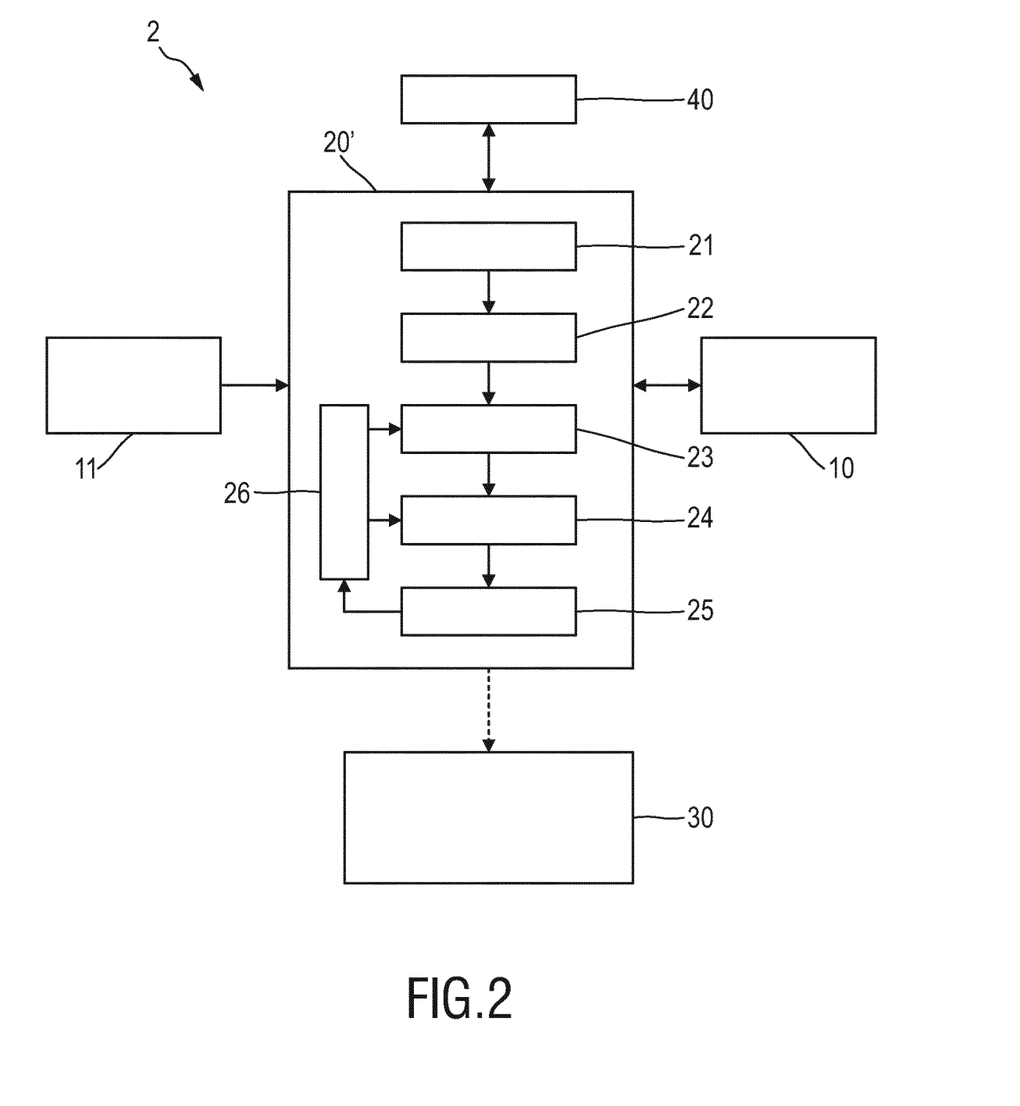
FIG. 2 shows a schematic diagram of a second embodiment of a system and a device according to the present invention.

FIG. 2 shows a schematic diagram of a second embodiment of a system 2 and a device 20' according to the present invention. A flowchart of an embodiment of a method, which may be performed by said device 20' is depicted in FIG. 3.

In addition to the elements of the first embodiment of the device 20, the second embodiment of the device 20' comprises a controller 26 for controlling the detector 23 and the evaluator 24 to repeat their operations one or more times with different pieces of expected anatomical feature information if the generated consistency is lower than the predetermined consistency threshold or another predetermined consistency threshold.

Figure 3:
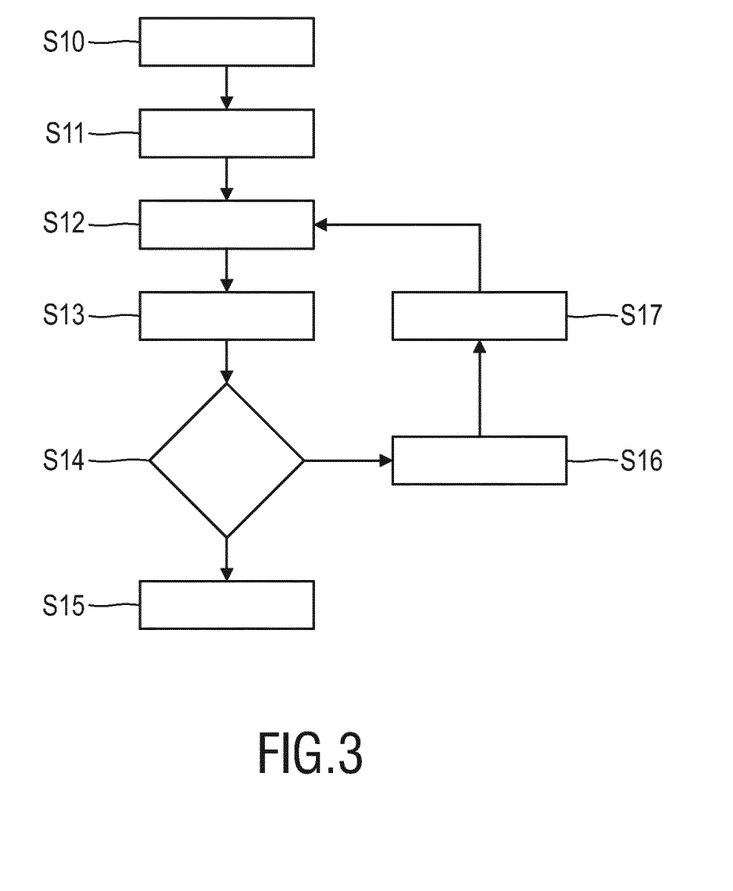
FIG. 3 shows a flow chart of an embodiment of a method according to the present invention.

As shown in FIG. 3, in a first step S10 a medical image and associated image-related information are obtained. One or more pieces of image-related information are then translated into expected anatomical feature information in a second step S11. In a third step S12 the expected anatomical feature information is searched in the obtained medical image or one or more given anatomical features are detected in the obtained medical image, which are then compared with the expected anatomical feature information. In a fourth step S13 the result of the third step is evaluated to generate a consistency measure indicating the consistency of the image-related information with the associated medical image.

In one embodiment it is checked in a fifth step S14 if the generated consistency is lower than a predetermined consistency threshold. If the generated consistency is higher than a predetermined consistency threshold, in step S15 the medical image and the image-related information are stored in the archive 10 or marked as verified, and optionally a corresponding consistency indication is issued. Otherwise, in step S16 an inconsistency indication is outputted.

Furthermore, using the device 20', another iteration of the steps S12 and S13 of the detector 23 and the evaluator 24 is performed. Hereby, alternative anatomical features are selected in step S17, which are provided to the detector 23. The detector 23 then searches the alternative anatomical feature information in the obtained medical image or detects one or more given anatomical features in the obtained medical image and compares them with alternative anatomical feature information. The evaluator 24 then evaluates the result of the detector 23 to generate an alternative consistency measure indicating the consistency of the alternative image-related information with the associated medical image. Finally, the output interface 25 outputs an inconsistency indication if the previously generated consistency measure and the alternative consistency measure are lower than a predetermined consistency threshold. In this case, one or more further iterations may be performed with still other sets of anatomical features as input to the detector 23. Further, in an embodiment, if the set of anatomical features has been exploited, the feature with the highest consistency will be selected as representing the most likely anatomy.

For instance, in an exemplary implementation, if the expected landmarks are detected but detection confidence is low, or the location of spatial relation of the landmarks does not comply with the learned distribution, a set of alternative detection algorithms matching related but different image-related information can be performed on the image to determine confidence in each of these alternatives. E.g., if detection algorithms fail to detect landmarks consistent with Body Part=breast, View Position=MLO and Laterality=right, the image will be tested for "Laterality=left" and/or "View Position"="CC" or "ML". The image can even be tested for "Body part"="calibration phantom". If any of these alternative descriptions has higher consistency with the image content than the original image-related information, an alert may be raised to the user, suggesting to double check the provided entries and proposing the alternative set of image-related information.

The present invention may be part of an image processing or image administration software or workflow, e.g. in the form of a verification tool, and may comprise a user interface. After the application of the method, the user may be prompted to accept or reject the automatically generated volume or the alternative image-related information that is automatically suggested by the system.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable non-transitory medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A device for verifying image-related information of a medical image, said device comprising:
    an image input for obtaining a medical image and associated image-related information accompanying or arising out of the medical image,
    a translator for translating one or more pieces of the image-related information into expected anatomical feature information,
    a detector for searching the expected anatomical feature information in the obtained medical image or for detecting one or more given anatomical features in the obtained medical image and comparing them with the expected anatomical feature information,
    an evaluator for evaluating the result of the detector to generate a consistency measure indicating the consistency of the image-related information with the associated medical image, and
    an output interface for outputting an inconsistency indication if the generated consistency measure is lower than a predetermined consistency threshold.

2. The device as claimed in claim 1,
    wherein said detector is configured to generate a confidence measure indicating the confidence, with which one or more pieces of expected anatomical feature information have been detected in the obtained medical image or with which one or more given anatomical features in the obtained medical image correspond with the expected anatomical feature information, and wherein said evaluator is configured to use the generated confidence measure in the generation of the consistency measure.

3. The device as claimed in claim 2,
    wherein said detector is configured to perform the detection separately for expected anatomical feature information from two or more pieces of image-related information to generate a confidence measure per piece of image-related information and wherein said evaluator is configured to combine the generated confidence measures for the generation of the consistency measure.

4. The device as claimed in claim 2,
    wherein said translator is configured to separately translate each of two or more pieces of image-related information into separate pieces of expected anatomical feature information, wherein said detector is configured to perform the detection separately for two or more pieces of expected anatomical feature information to generate a confidence measure per piece of image-related information and wherein said evaluator is configured to combine the generated confidence measures for the generation of the consistency measure.

5. The device as claimed in claim 1,
wherein said translator is configured to translate one or more pieces of image-related information into expected anatomical feature information including the number and/or kind of anatomical features, expected image properties, distribution and/or location of one or more expected anatomical features, and/or variability in the spatial relations of one or more expected anatomical features.

6. The device as claimed in claim 1,
further comprising a controller for controlling the detector and the evaluator to repeat their operations one or more times with different pieces of expected anatomical feature information if the generated consistency is lower than the predetermined consistency threshold or another predetermined consistency threshold.

7. The device as claimed in claim 1,
wherein said translator is configured to access a database storing separate expected anatomical feature information for a plurality of pieces of image-related information for translating one or more pieces of image-related information into expected anatomical feature information.

8. The device as claimed in claim 7,
wherein said translator is configured to access a database storing the number and/or kind of anatomical features, expected image properties, distribution and/or location of one or more expected anatomical features, and/or variability in the spatial relations of one or more expected anatomical features.

9. The device as claimed in claim 7,
wherein said translator is configured to access a database storing separate expected anatomical feature information obtained by learning from training medical images and correctly associated image-related information.

10. The device as claimed in claim 6,
wherein said detector is configured to search alternative anatomical feature information in the obtained medical image or to detect one or more given anatomical features in the obtained medical image and compare them with alternative anatomical feature information,
wherein said evaluator is configured to evaluate the result of the detector to generate an alternative consistency measure indicating the consistency of the alternative image-related information with the associated medical image, and
wherein said output interface is configured to output an inconsistency indication if the previously generated consistency measure and the alternative consistency measure are lower than a predetermined consistency threshold.

11. The device as claimed in claim 1,
wherein said image input is configured to obtain a medical image file comprising a data part including the medical image and a header including associated image-related information, in particular a medical image file in accordance with the DICOM standard.

12. The device as claimed in claim 1,
wherein said output interface is configured to output an inconsistency indication in the form of an alert, in particular including the degree of inconsistency.

13. A method for verifying image-related information of a medical image, said method comprising:
obtaining a medical image and associated image-related information arising out of the medical image,
translating one or more pieces of the image-related information into expected anatomical feature information,
searching the expected anatomical feature information in the obtained medical image or detecting one or more given anatomical features in the obtained medical image, which are then compared with the expected anatomical feature information,
evaluating the result of the step of searching or detecting to generate a consistency measure indicating the consistency of the image-related information with the associated medical image, and
outputting an inconsistency indication if the generated consistency measure is lower than a predetermined consistency threshold.

14. A computer program comprising program code means for causing a computer to carry out the steps of the method as claimed in claim 13 when said computer program is carried out on the computer.

15. The method as claimed in claim 13, wherein the associated image-related information is a body part, image laterality, imaging position of the subject, view position, type of imaging system, or parameter or setting of image acquisition equipment.

16. The method as claimed in claim 13 wherein the expected anatomical feature information is a landmark, contour, distance information, size information, anatomical feature identification, shape descriptor, or model pose.

17. The method as claimed in claim 13, wherein the consistency measure indicates a correctness of the image-related information.

18. A method for verifying the correctness of image-related information of a medical image, said method comprising:
receiving a medical image and associated image-related information derived from the medical image,
translating one or more pieces of the image-related information into expected anatomical feature information,
searching the expected anatomical feature information in the received medical image or detecting one or more given anatomical features in the received medical image, which are then compared with the expected anatomical feature information,
evaluating the result of the step of searching or detecting to generate a consistency measure indicating the consistency of the image-related information with the associated medical image, and
storing the image-related information if the consistency measure is higher than a predetermined consistency threshold and verifies the correctness of the image-related information.

19. The method according to claim 18, wherein the associated image-related information is received as a part of or during the acquisition of the medical image.

20. The method according to claim 13, wherein the associated image-related information is obtained as a part of or during the acquisition of the medical image.

* * * * *